(12) United States Patent
Fridag et al.

(10) Patent No.: US 10,562,833 B2
(45) Date of Patent: Feb. 18, 2020

(54) METHOD FOR OBTAINING ALCOHOLS FROM ALDEHYDES III

(71) Applicant: Evonik Degussa GmbH, Essen (DE)

(72) Inventors: Dirk Fridag, Haltern am See (DE); Robert Franke, Marl (DE); Michael Grass, Haltern am See (DE); Florian Boeck, Düsseldorf (DE); Corinna Hecht, Haltern am See (DE); Benedikt Dercks, Bochum (DE); Udo Lenz, Recklinghausen (DE); Christoph Hiller, Dülmen (DE); Christoph Ehlers, Münster (DE); Stefan Münzner, Dorsten (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 16/204,263

(22) Filed: Nov. 29, 2018

(65) Prior Publication Data

US 2019/0169105 A1    Jun. 6, 2019

(30) Foreign Application Priority Data

Dec. 1, 2017   (EP) ..................................... 17205017

(51) Int. Cl.
*C07C 29/141*   (2006.01)
*C07C 29/17*    (2006.01)
(Continued)

(52) U.S. Cl.
CPC ............ *C07C 29/141* (2013.01); *B01J 31/185* (2013.01); *C07C 29/175* (2013.01); *C07C 29/80* (2013.01);
(Continued)

(58) Field of Classification Search
CPC ....... C07C 29/80; C07C 29/82; C07C 29/141; C07C 29/175; C07C 45/50; C07C 45/74; C07C 45/82; B01J 2531/822; B01J 31/185
See application file for complete search history.

(56) References Cited

U.S. PATENT DOCUMENTS 6,280,593 B1   8/2001   Wiese et al.
6,284,116 B1   9/2001   Wiese et al.
(Continued)

FOREIGN PATENT DOCUMENTS

DE   4243524 A1    6/1994
DE   198 49 922 A1   5/2000
(Continued)

OTHER PUBLICATIONS

Fridag et al., U.S. Appl. No. 16/203,929, filed Nov. 29, 2018.
(Continued)

*Primary Examiner* — Yate' K Cutliff
(74) *Attorney, Agent, or Firm* — Philip P. McCann; Nexsen Pruet PLLC (57) ABSTRACT

The present invention relates to a method for preparing saturated $C_n$- and $C_{2n}$-alcohols, wherein the ratio of $C_n$- to $C_{2n}$-alcohols is controlled by a distillative separation of the aldehydes used.

20 Claims, 4 Drawing Sheets

(51) Int. Cl.
  *B01J 31/18*   (2006.01)
  *C07C 45/82*   (2006.01)
  *C07C 45/74*   (2006.01)
  *C07C 29/82*   (2006.01)
  *C07C 29/80*   (2006.01)
  *C07C 45/50*   (2006.01)
  C07C 31/12    (2006.01)
  C07C 31/125   (2006.01)
  C07C 47/02    (2006.01)
  C07C 47/21    (2006.01)

(52) U.S. Cl.
  CPC .......... *C07C 29/82* (2013.01); *C07C 45/50* (2013.01); *C07C 45/74* (2013.01); *C07C 45/82* (2013.01); *B01J 2231/643* (2013.01); *B01J 2531/822* (2013.01); *C07C 31/12* (2013.01); *C07C 31/125* (2013.01); *C07C 47/02* (2013.01); *C07C 47/21* (2013.01)

(56) References Cited

U.S. PATENT DOCUMENTS

| | | | |
|---|---|---|---|
| 6,303,535 B1 | 10/2001 | Scholz et al. | |
| 6,340,778 B1 | 1/2002 | Bueschken et al. | |
| 6,455,743 B1* | 9/2002 | Ueda | C07C 29/141 568/451 |
| 6,482,972 B1 | 11/2002 | Bahrmann et al. | |
| 6,511,583 B1 | 1/2003 | Mueller et al. | |
| 8,455,701 B2 | 6/2013 | Kaizik et al. | |
| 8,563,782 B2 | 10/2013 | Kaizik et al. | |
| 8,581,008 B2* | 11/2013 | Kaizik | C07C 45/74 568/461 |
| 8,871,985 B2* | 10/2014 | Van Vliet | C07C 29/141 568/451 |
| 9,567,276 B2 | 2/2017 | Klasovsky et al. | |
| 9,676,805 B2 | 6/2017 | Dyballa et al. | |
| 9,845,276 B2 | 12/2017 | Franke et al. | |
| 9,914,681 B2 | 3/2018 | Geilen et al. | |
| 10,000,440 B2 | 6/2018 | Reeker et al. | |
| 2002/0133047 A1 | 9/2002 | Bahrmann et al. | |
| 2010/0048959 A1 | 2/2010 | Sigl et al. | |
| 2012/0004473 A1 | 1/2012 | Lee et al. | |
| 2012/0123169 A1 | 5/2012 | Kaizik et al. | |
| 2012/0253083 A1* | 10/2012 | Kaizik | C07C 29/175 568/881 |
| 2016/0075621 A1* | 3/2016 | Hashmi | B01J 19/00 560/99 |
| 2016/0236150 A1 | 8/2016 | Geilen et al. | |
| 2016/0257634 A1 | 9/2016 | Dyballa et al. | |
| 2017/0129838 A1* | 5/2017 | Dyballa | C07C 47/02 |
| 2018/0126361 A1 | 5/2018 | Klasovsky et al. | |
| 2018/0208541 A1 | 7/2018 | Boeck et al. | |
| 2018/0319727 A1 | 11/2018 | Dyballa et al. | |

FOREIGN PATENT DOCUMENTS

| | | |
|---|---|---|
| DE | 198 49 924 A1 | 5/2000 |
| DE | 199 14 259 A1 | 10/2000 |
| DE | 199 33 348 A1 | 2/2001 |
| DE | 19957522 A1 | 5/2001 |
| DE | 699 16 755 T2 | 4/2005 |
| DE | 6991675 T2 | 4/2005 |
| DE | 10 2009 001 594 A1 | 9/2010 |
| DE | 10 2009 045 139 A1 | 3/2011 |
| DE | 10 2009 045 718 A1 | 4/2011 |
| EP | 1004563 A2 | 5/2000 |
| EP | 2796440 A1 | 10/2014 |
| EP | 3037400 A1 | 6/2016 |
| WO | 2017/080690 A1 | 5/2017 |

OTHER PUBLICATIONS

Fridag et al., U.S. Appl. No. No. 16/204,572, filed Nov. 29, 2018.
Premkumar et al., "Retrofitting Conventional Column Systems to Dividing-Wall Columns," Chemical Engineering Research and Design, Elsevier, copyright 2009, vol. 87, pp. 47-60 (14 pages).
Yildirim et al., "Dividing Wall Columns in Chemical Process Industry: A Review On Current Activities," Separation and Purification Technology, Elsevier, copyright 2011, vol. 80, pp. 403-417 (15 pages).
Fridag et al., U.S. Appl. No. 16/204,572, filed Nov. 29, 2018.
Reeker et al., U.S. Appl. No. 15/925,401, filed Mar. 19, 2018.
European Search Report dated Apr. 8, 2019 in EP 18209425.0 (11 pages).

* cited by examiner

METHOD FOR OBTAINING ALCOHOLS FROM ALDEHYDES III

CROSS REFERENCE TO RELATED APPLICATIONS

This application claims priority pursuant to 35 U.S.C. § 119 to European Patent Application No. 17205017.0, filed Dec. 1, 2017, which is incorporated herein by reference in its entirety.

FIELD

The present invention relates to a method for preparing $C_n$- and $C_{2n}$-alcohols, wherein the ratio of $C_n$- to $C_{2n}$-alcohols is controlled by a distillative separation of the aldehydes used.

BACKGROUND

Alcohols fill an important role in industry. They are often used as intermediates for the preparation of lubricant oils, fats, plasticizers, pharmaceuticals, cosmetics and flavourings. Alcohols are also used directly as solvents, antifreeze agents or fuel additives.

Plasticizers are used in large amounts for modifying the thermoplastic properties of numerous industrially important products such as plastics for example, but also paints, coating compositions, sealants etc. An important class of plasticizers are the ester plasticizers which include, inter alia, phthalic esters, trimellitic esters, phosphoric esters etc. The alcohols used for producing ester plasticizers are generally referred to as plasticizer alcohols. To produce ester plasticizers having good performance properties, there is a need for plasticizer alcohols having about 5 to 12 carbon atoms.

Due to the phthalate discussion in the plasticizer sector, the demand for novel phthalate-free plasticizers is increasing. It is critical in this case, however, that the respective plasticizers must meet narrow specifications with regard to their properties with respect to the applications. Examples here include the viscosity or the volatility of the plasticizers. Control of the essential properties of the plasticizers depends in this case less on the esterification reaction typically used in the production of plasticizers but rather on the raw materials used, especially the alcohols used. Essential factors here are, for example, the number of carbon atoms of the alcohols used or the isomer distribution thereof. For this purpose, alcohols having 4, 5 or 6 carbon atoms for example are suitable. At the same time, however, it is also necessary to produce the C8-, C10- and C12-alcohols described.

One of the best-known routes to alcohols is the hydroformylation reaction in which alkenes are converted to aldehydes, which are then subjected to a hydrogenation, in order to produce the corresponding alcohols ($C_n$-alcohols). An exception here is the hydroformylation of propene and unbranched butenes. Here, the resulting aldehydes are usually subjected to a further reaction step, the aldolization, in order to produce long-chain unsaturated aldehydes. These are then also subjected to a hydrogenation and the longer-chain alcohols (C2n-alcohols) obtained are used for the most part in the production of phthalate-containing plasticizers.

For instance, EP 1004563 describes the preparation of alcohols by hydroformylation of an olefin, aldol condensation of a portion of the aldehyde and subsequent hydrogenation reaction. However, specific control of the composition of the alcohols obtained is not possible in this manner.

The challenge that arises therefrom is on the one hand to control the isomer distribution of the alcohols to be produced, and on the other hand however also to control especially the ratio of $C_n$- to $C_{2n}$-alcohols.

SUMMARY

The object of the present invention is to provide a method which meets the requirements mentioned above and allows the selective control of the composition of the resulting alcohols.

The object of the present invention is achieved by a method for preparing $C_n$- and $C_{2n}$-alcohols, wherein the ratio of $C_n$- to $C_{2n}$-alcohols is determined by selective control of the reactant streams of aldolization and hydrogenation.

DETAILED DESCRIPTION

Accordingly, the present invention relates to a method for preparing saturated $C_n$- and $C_{2n}$-alcohols where n=4, 5 and 6 comprising the method steps of a) providing a mixture of isomeric $C_n$-aldehydes where n=4, 5 and 6, wherein the proportion of unbranched aldehydes is at least 20% by weight, based on the $C_n$-aldehydes provided where n=4, 5 and 6, b) carrying out a distillation for the at least partial separation of the isomeric $C_n$ aldehydes where n=4, 5 and 6 into a first stream having a higher proportion of linear aldehydes than the mixture provided in a) and into a second stream having a higher proportion of branched aldehydes than the mixture provided in a)

c) carrying out an aldol condensation of the aldehydes present in the first stream having a higher proportion of linear aldehydes than the mixture provided in a) to obtain a mixture of $C_n$- and $\alpha,\beta$-unsaturated $C_{2n}$-aldehydes d) mixing the mixture of $C_n$- and $\alpha,\beta$-unsaturated $C_{2n}$-aldehydes obtained in c) with the second stream, provided in b), having a higher proportion of branched Cn aldehydes where n=4, 5 and 6 than the mixture provided in a)

e) hydrogenating the mixture of $C_n$- and $\alpha,\beta$-unsaturated $C_{2n}$-aldehydes and $C_n$-aldehydes where n=4, 5 and 6 obtained in d) with hydrogen to obtain a mixture of saturated $C_n$ and $C_{2n}$-alcohols and f) separating the mixture of $C_n$ and $C_{2n}$-alcohols.

The process chain according to the invention allows, in a surprising manner, the preparation of saturated $C_n$ and $C_{2n}$-alcohols which may be used directly for the production of plasticizers. It has been found particularly in this case that the isomer distribution, for example of the $C_n$-alcohols, is such that these result in plasticizers after esterification which have an advantageous spectrum of properties and the water content of the Cn alcohols is so low that these can be used without further pretreatment in anhydride esterification reactions or transesterifications.

Figure 1:
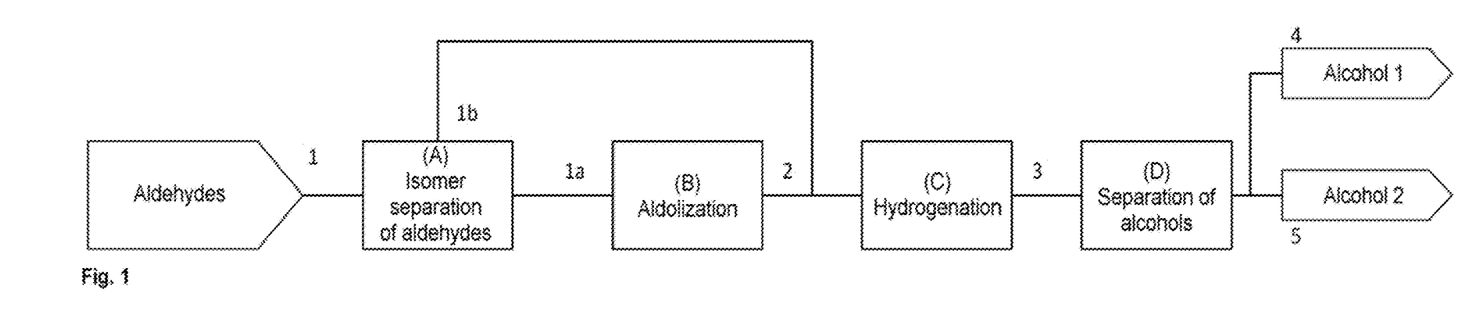
FIG. 1 is a schematic of a method according to one or more embodiments described herein.

The basic sequence of the method according to the invention is shown in FIG. 1. In the first step, a stream composed of isomeric $C_n$-aldehydes where n=4, 5 and 6 is provided (1) and is separated distillatively into a first stream (1a) having a higher proportion of linear aldehydes than the mixture provided in a) and into a second stream (1b) having a higher proportion of branched aldehydes than the mixture provided in a). The first stream (1a) comprising isomeric $C_n$-aldehydes where n=4, 5 and 6 having a higher proportion of linear aldehydes is introduced into a reactor for the purpose of carrying out an aldol condensation to obtain a mixture of $C_n$- and α,β-unsaturated $C_{2n}$-aldehydes. The product stream obtained from the aldol condensation comprising a mixture of $C_n$- and α,β-unsaturated $C_{2n}$-aldehydes is mixed with the stream (1b) obtained in the context of distillative separation comprising isomeric $C_n$-aldehydes where n=4, 5 and 6 having a higher proportion of branched aldehydes and is transferred as reactant stream (2) into a further reactor for the purpose of carrying out a hydrogenation of the mixture of $C_n$- and α,β-unsaturated $C_{2n}$-aldehydes and isomeric $C_n$-aldehydes where n=4, 5 and 6 (reactant stream (2)) with hydrogen to obtain a mixture of saturated $C_n$ and $C_{2n}$-alcohols. The respective fractions with Cn and C2n alcohols as main components are obtained from this mixture by thermal separation.

In principle, all $C_n$-aldehydes where n=4, 5 and 6 known to those skilled in the art are suitable, either in pure form or in the form of mixtures, for use in the method according to the present invention, wherein a basic prerequisite is that the proportion of unbranched aldehydes is at least 20% by weight, based on the $C_n$-aldehydes used where n=4, 5 and 6.

In particular in the method according to the invention, aldehyde streams of identical chain length are used. The proportion of unbranched aldehydes is at least 20% by weight, based on the $C_n$-aldehydes used where n=4, 5 and 6, preferably at least 40% by weight. In particular, the proportion of unbranched aldehydes is 40 to 99.5% by weight, especially preferably the proportion of unbranched aldehydes is 95-99.5% by weight, based on the $C_n$-aldehydes used where n=4, 5 and 6.

In the context of industrial scale processes, many such aldehydes or mixtures thereof are obtained from the corresponding olefins by hydroformylation.

Accordingly, in a preferred embodiment of the present invention, the $C_n$-aldehydes where n=4, 5 and 6 provided in step a) are prepared by hydroformylation of isomeric olefins having 3 to 5 carbon atoms with synthesis gas in the presence of a hydroformylation catalyst to form the aldehydes specified. Appropriate hydroformylation methods are known to those skilled in the art and are described by way of example in Hydroformylation Fundamentals, Processes and Applications in Organic Synthesis Volume 1 & 2 Edition 1, Franke, Borner, Willey VCH Verlag GmbH & Co.

Generally, the process is operated with rhodium or cobalt catalysts and also with or without complex-stabilizing additives such as organic phosphines or phosphites. The temperatures and pressures may be varied within wide limits depending on the catalyst or olefin. A description of the hydroformylation of olefins is found for example in J. Falbe, New Syntheses with Carbon Monoxide, Springer-Verlag, Heidelberg-New York, 1980, pages 99 ff. and in Kirk-Othmer, Encyclopedia of Chemical Technology, Volume 17, 4th Edition, John Wiley & Sons, pages 902 to 919 (1996).

The reaction mixtures of the hydroformylation are advantageously firstly freed from the catalyst prior to use in the method according to the invention. If a cobalt catalyst has been used, this can be accomplished by releasing pressure, oxidation of the cobalt carbonyl compounds remaining in the hydroformylation mixture in the presence of water or aqueous acid and removal of the aqueous phase. Decobalting processes are well known, see for example J. Falbe, loc. cit., Kirk-Othmer, loc. cit., 164, 175, BASF-Verfahren.

If a rhodium compound is used as hydroformylation catalyst, it can be removed, for example, by thin-film evaporation as distillation residue.

In the preferred embodiment of the present invention, the hydroformylation is carried out according to the method described in WO 2017/080690.

In this case, in the hydroformylation a catalyst system is used which comprises rhodium as central atom and is complexed with the ligand (1):

(1)

The IUPAC designation for ligand (1) is 3,3'-di-tert-butyl-5,5'-dimethoxy-[1,1'-biphenyl]-2,2'-diyltetrakis(2,4-dimethylphenyl)bis(phosphite).

The hydroformylation is effected in particular at a temperature between 120° C. and 140° C. The pressure is preferably between $15*10^5$ Pa and $25*10^5$ Pa.

To increase operating duration, the hydroformylation is performed in the presence of an organic amine of formula (2)

(2)

in which Ra, Rb, Rc, Rd, Re and Rf represent identical or different hydrocarbon radicals which may also be bonded to one another. The organic amine preferably comprises at least one 2,2,6,6-tetramethylpiperidine unit. Specifically the organic amine may be a di-4-(2,2,6,6-tetramethylpiperidinyl) sebacate.

It is recommended to establish a rhodium concentration in the first reaction mixture between 1 ppmw and 1000 ppmw. The ligand/rhodium ratio should be between 1:1 to 100:1 and no further ligand is to be provided as part of the homogeneous catalyst system in addition to the organophosphorus compound according to formula (1). In industrial operation it cannot be ruled out that owing to impurities organophosphorus compounds other than 3,3'-di-tert-butyl-5,5'-dimethoxy-[1,1'-biphenyl]-2,2'-diyltetrakis(2,4-dimethylphenyl)bis(phosphite) complex to the rhodium as part of the catalyst system. However, such impurities can be disregarded at the indicated ligand/rhodium ratio. This statement relates solely to ligand (1) and no further ligand need be intentionally provided.

The isomeric $C_n$-aldehydes used in the method according to the invention where n=4, 5 and 6 are separated at least partially by means of a distillation of the isomeric Cn aldehydes where n=4, 5 and 6 according to step b) into a first stream (1a) having a higher proportion of linear aldehydes than the mixture provided in a) and into a second stream (1b) having a higher proportion of branched aldehydes than the mixture provided in a).

The stream is divided via a rectification column. This is effected according to the prior art and separates the feed (1) into the two individual streams (1a) and (1b).

The ratios between (1a) and (1b) are selected such that the desired amount of $C_{2n}$ alcohol and $C_n$ alcohol of the desired isomer distribution are formed according to the following approach:

$$\text{Mass stream } C_{2n} \text{ alcohol}(5) = Feed*Split* \\ (Xn\_Aldol*FeedS\_w\_n + Xi\_Aldol*FeedS\_w\_i)* \\ (2*M\_Cn\_al - 18)/(2*M\_Cn\_al + 2)* \\ X\_Hydr*X\_Dist$$

$$\text{Mass stream } Cn \text{alcohol}(4) = Feed*Split*((1-Xn\_Aldol)*FeedS\_w\_n) + Feed*(1-Split)*FeedD\_w\_n/ \\ M\_Cn\_al*M\_Cn\_ol*X\_n\_Hydr*X\_n\_Dist + \\ Feed*Split*((1-Xi\_Aldol)*FeedS\_w\_i) + Feed* \\ (1-Split)*FeedD\_w\_i/ \\ M\_Cn\_al*M\_Cn\_ol*X\_i\_Hydr*X\_i\_Dist$$

$$\text{Mass stream}(1b) = Feed*(1-Split)$$

$$\text{Proportion of linear alcohols}(4) = Feed*Split*((1-Xn\_Aldol)*FeedS\_w\_n) + Feed*(1-Split)*FeedD\_w\_n/ \\ M\_Cn\_al*M\_Cn\_ol*X\_n\_Hydr*X\_n\_Disti \\ (Feed*Split*((1-Xn\_Aldol)*FeedS\_w\_n) + Feed* \\ (1-Split)*FeedD\_w\_n/ \\ M\_Cn\_al*M\_Cn\_ol*X\_n\_Hydr*X\_n\_Dist + \\ Feed*Split*((1-Xi\_Aldol)*FeedS\_w\_i) + Feed* \\ (1-Split)*FeedD\_w\_i/ \\ M\_Cn\_al*M\_Cn\_ol*X\_i\_Hydr*X\_i\_Dist)$$

Feed=feed (1)
Split=percentage proportion (1a) based on feed (1)
FeedS_w_n=percentage concentration of linear aldehydes Cn in stream (1a)
FeedS_w_i=percentage concentration of branched aldehydes Cn in stream (1a)
FeedD_w_n=percentage concentration of linear aldehydes Cn in stream (1b)
FeedD_w_i=percentage concentration of branched aldehydes Cn in stream (1b)
Xn_Aldol=yield of C2n aldolization product based on the linear aldehydes Cn in the aldolization (B)
Xi_Aldol=yield of C2n aldolization product based on the branched aldehydes Cn of the aldolization (B)
M_Cn_al=molar mass of the aldehydes Cn
X_Hydr=yield of C2n aldolization products hydrogenated to the corresponding alcohols
X_Dist=yield of C2n alcohols in the distillation
X_n_Hydr=yield of linear Cn aldehydes hydrogenated to the corresponding alcohols
X_i_Hydr=yield of branched Cn aldehydes hydrogenated to the corresponding alcohols X_n_Dist=yield of linear Cn alcohols in the distillation
X_i_Dist=yield of branched Cn alcohols in the distillation The isomer distribution of the $C_n$ alcohols can still be shifted within limits by the use of thermal separation. For this purpose, the following applies for controlling the amount, based only on the adjusted mass streams of $C_n$ alcohol.

$$M\_Dist = -1*(M\_Feed*(Prod\_w\_n - Feed\_w\_n)/(Dist\_w\_n - Prod\_w\_n))$$

In this case the following limits apply $$Dist\_w\_n < Feed\_w\_n < Prod\_w\_n$$

Figure 2:
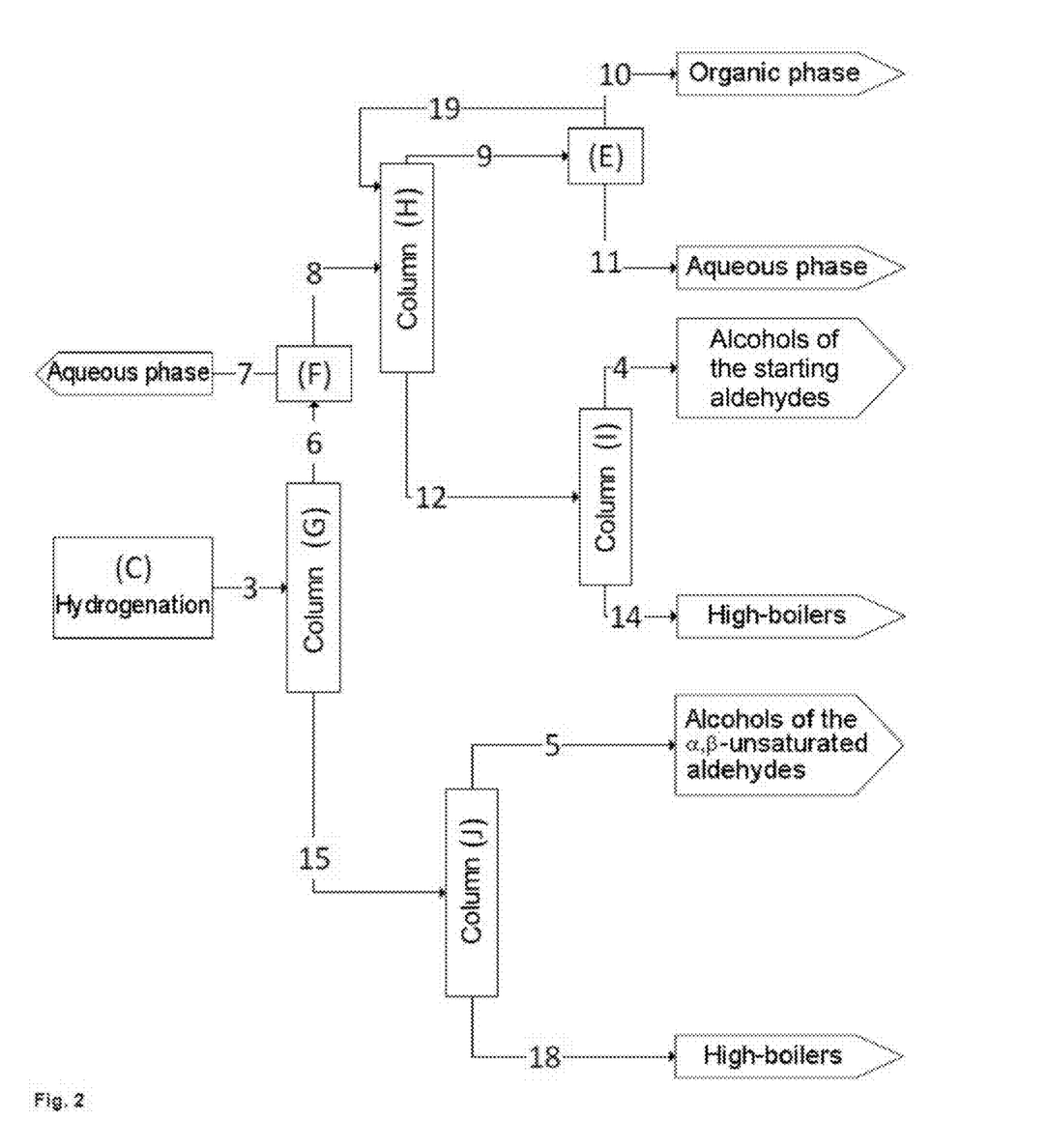
FIG. 2 is a schematic of a method according to one or more embodiments described herein.
Figure 3:
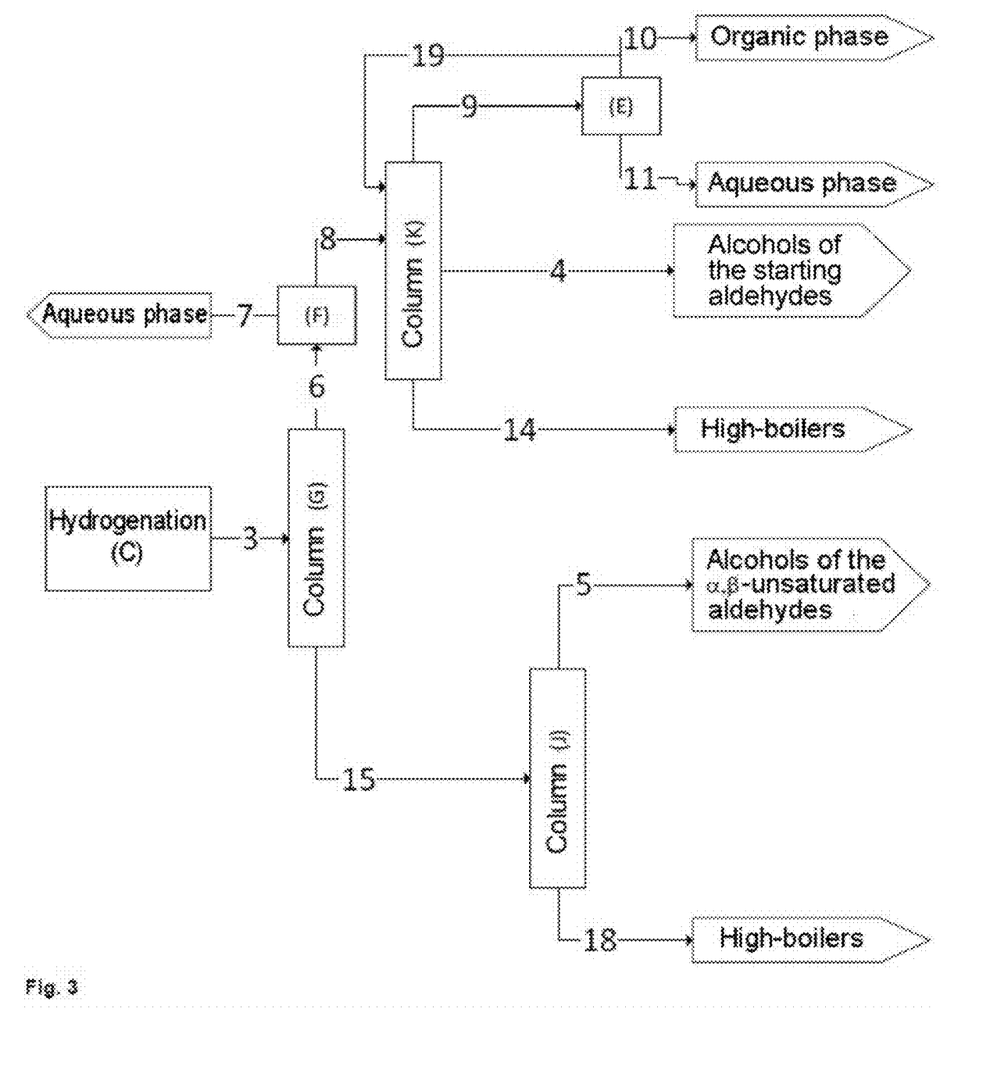
FIG. 3 is a schematic of a method according to one or more embodiments described herein.

M_Feed=mass stream of Cn alcohols
Prod_w_n=percentage concentration of linear aldehydes Cn of product ((4) in FIGS. 2&3))
Feed_w_n=percentage concentration of linear aldehydes Cn of feed ((8) in FIGS. 2&3))
Dist_w_n=percentage concentration of linear aldehydes Cn of distillate ((10) in FIGS. 2&3))
M_Dist=mass stream of Cn alcohols to be discharged ((10) in FIGS. 2&3))

All positions refer only to the alcohol components; secondary components are not considered and are subtracted from the mass streams.

In accordance with the invention, the isomeric $C_n$-aldehydes where n=4, 5 and 6 in stream (1a) are converted by aldol condensation, particularly in the presence of aqueous sodium hydroxide solution, to a mixture of $C_n$- and α,β-unsaturated $C_{2n}$-aldehydes. Appropriate processes are known, for example, from DE19957522A1, DE102009045139A1, DE102009001594A1.

The aldol condensation is particularly preferably carried out in a tubular reactor which comprises at least one mixing module which disperses the reactant aldehyde into droplets having an average diameter (Sauter diameter) of 0.2 mm to 2 mm in the continuous catalyst phase (process liquor), which consists of aqueous sodium hydroxide solution and sodium salts of carboxylic acids and has a sodium content of 0.6 to 1.75% by mass and a pH in the range from 12.5 to 13.5.

To form the process liquor, aqueous sodium hydroxide solution is used in the method according to the invention. The aqueous sodium hydroxide solution forms the process liquor together wih the return liquor. The return liquor comprises, as well as sodium hydroxide, sodium salts of carboxylic acids, principally of pentanoic acids. The carboxylic acid salts have been formed essentially by the Cannizzaro reaction.

In the method according to the invention, the sodium content of the process liquor at the reactor inlet is 0.60 to 1.75% by mass, especially 1.1 to 1.20% by mass. To adjust the sodium concentration of the process liquor, aqueous sodium hydroxide solution is fed into the return liquor at a concentration greater than 2.5% by mass. In order to introduce little water into the reaction system, preference is given to using aqueous sodium hydroxide solution at a relatively high concentration. In the method according to the invention, preference is given to using aqueous sodium hydroxide solution in the concentration range from 5 to 30% by mass, for example at 10% by mass.

The method according to the invention is performed in a tubular reactor which has at least one mixing module, preferably more than one mixing module. In particular, the number of mixing modules is 1 to 30, very particularly 10 to 20.

A mixing module means a static mixer, i.e. a passive component which has no direct intrinsic energy requirement.

The tubular reactor consists of a tube which is preferably aligned vertically. The flow through it may be from bottom to top or vice versa. An industrial reactor may also consist of a plurality of tubes arranged in parallel, which are connected to one another by U-tubes.

A mixing module is preferably present at the reactor inlet. Voids are present between the mixing modules. The proportion by volume of the total volume of the reactor outside the mixing module(s) is 20 to 80%, especially 30 to 60%. The mixing modules may have equal or different distances from one another. The distance between the mixer modules preferably decreases in the direction of flow. The distances of the mixer modules from one another are, depending on the intended superficial velocity, the phase ratio between reactant and catalyst phases, the reaction progress and the mixer type, 0.2 to five times the mixing module length, especially 0.5 to two times the mixing module length.

The mixing module consists of a static mixer or of an arrangement of two or more, preferably two, static mixers.

When the mixer module consists of two identical static mixers, these are preferably arranged twisted about the longitudinal axis of the reactor, especially twisted by an angle of 45° up to 90°. Mixing elements are preferably arranged in the mixer module at a distance of two tube diameters.

A mixing module may also consist of static mixers of different design. It may be advantageous that, in the case of a mixer module consisting of two static mixers, the first has a lower hydraulic diameter than the second. In this case, the first static mixer produces very small droplets and the second static mixer, as a result of selection of a greater hydraulic diameter, prevents the coalescence of the cluster of droplets.

The hydraulic diameter of the mixing elements of the mixer modules preferably decreases in the direction of flow.

The mixer modules may be the same or different in the reactor, i.e. they may be of the same or different design.

The mixing elements used may be all static mixers which, under the intended reaction conditions, are capable of dispersing the organic phase in the catalyst phase into droplets with an average Sauter diameter in the range from 0.2 to 2.0 mm.

The static mixers used in the method according to the invention may be mixing elements which are suitable for the dispersion of two immiscible low-viscosity liquids, as are commercially available. In accordance with the invention, the aldol condensation of the $C_n$-aldehydes is carried out in the temperature range from 100 to 150° C., more particularly in the range from 110 to 140° C., especially preferably in the range from 120 to 140° C.

The reaction may be carried out isothermally, adiabatically or polytropically in the temperature ranges specified. For example, the temperature at the reactor inlet may be 120° C. and the temperature at the reactor outlet may be 140° C.

The reaction pressure in the reactor is at least high enough so that both the process liquor and the organic substances (reactant and products) are each present as a liquid phase. The pressure is in the range from 0.2 to 1.0 MPa, preferably in the range from 0.3 to 0.5 MPa.

In the method according to the invention, the ratio [kg/kg] of process liquor to reactant at the reactor inlet is in the range from 5 to 40, especially in the range from 10 to 15.

The average superficial velocity of the mixture of reactant and process liquor (assuming the same flow rate of both phases) in the industrial reactor is in the range from 0.5 to 4 m/s, especially in the range from 1 to 2.5 m/s.

The average residence time of the reaction mixture in the reactor is 40 to 360 s, especially 60 to 180 s.

In the method according to the invention, the droplets of the organic phase dispersed in the process liquor on leaving a mixer module have an average Sauter diameter of 0.2 to 2 mm, especially of 0.6 to 1.3 mm.

The load factor is in the range from 0.2 to 0.8.

The aldehydes obtained may optionally be processed prior to further use in the method according to the invention.

One way of doing so is to cool the reaction output and to separate the organic phase from the liquor phase. The phase separation is preferably effected in the temperature range from 60 to 130° C., particularly in the range from 70 to 120° C., very particularly in the range from 90 to 110° C. The separation times, depending on the temperature selected, are 3 to 10 minutes. At temperatures above 90° C., the separation time is less than 8 minutes. The separation time is defined as the time by which the organic product of value phase is clear and free of traces of heterogeneous water.

To separate the heavy, aqueous phase from the light organic phase, separators may be used which facilitate the phase separation using gravity alone. These so-called gravity separators may also be provided with internals as a coalescence-promoting measure to improve the separating performance. The use of internals accelerates the coalescence and sedimentation process. As coalescence aids, it is possible to use, for example, plates, random packings, mesh packings or fibre bed separators. Gravity separators can be configured as horizontal vessels or as upright vessels.

As an alternative to gravity separators, it is also possible to use separators operating according to the centrifugal principle for liquid-liquid separation. The heavy phase here is separated off by means of centrifugal forces in a rotating drum.

In order to separate off the heavy, aqueous phase in the method according to the invention, preference is given to using gravity separators, preferably gravity separators configured as horizontal vessels with internals.

Part of the liquor phase which has been separated off is discharged to remove water of reaction, and the other part is recirculated into the reactor. With the discharge stream, a portion of the carboxylic acids formed as by-products (as sodium salts) and sodium hydroxide are also removed. This stream can be sent to a wastewater treatment plant. However, it is also possible to work up this stream and partly recirculate it into the process, as described, for example, in DE 198 49 922 and DE 198 49 924.

If the organic phase, in addition to the $C_n$- and α,β-unsaturated $C_{2n}$-aldehydes, comprises other by-products such as carboxylic acid salts, sodium hydroxide and dissolved water, traces of base and a portion of the carboxylic acid salts can be removed by water scrubbing. The water extract obtained can be used to make up fresh base.

The $C_n$- and α,β-unsaturated $C_{2n}$-aldehydes thus obtained are mixed according to step d) with the second stream (1b) obtained in b), having a higher proportion of branched aldehydes than the mixture provided in a), to obtain a reactant stream (2).

The mixing of the two substreams is ensured by appropriate static or dynamic mixers, as is known to those skilled in the art. The two streams are preferably combined here by means of a static mixer such as, for example, the CompaX™ module from Sulzer. At this position, an appropriate pump may also serve as dynamic mixer.

The reactant stream (2) obtained by mixing comprises the $C_n$- and α,β-unsaturated $C_{2n}$-aldehydes obtained in the aldolization and the fraction obtained distillatively in step b)

comprising $C_n$-aldehydes where n=4, 5 and 6 having a higher proportion of branched aldehydes than the starting mixture in the form of a mixture. This mixture is hydrogenated with hydrogen according to step e) of the method according to the invention to obtain a mixture of saturated $C_n$ and $C_{2n}$-alcohols. The hydrogenation is likewise effected according to processes known per se, for example in the temperature range from 170° C. to 200° C. at a pressure of $15*10^5$ Pa to $30*10^5$ Pa over a supported catalyst which contains at least nickel and copper as active components, as known for example from EP3037400.

The hydrogenation catalyst preferably consists of a support material based on titanium dioxide, zirconium dioxide, aluminium oxide, silicon oxide or mixtures thereof, wherein hydrogenation-active metals, in particular at least one element from the group of copper, cobalt, nickel, chromium, are applied to this support material.

It is possible to use aluminium oxide, aluminosilicate, silicon dioxide, titanium dioxide, zirconium dioxide as support precursors. A preferred support precursor is aluminium oxide, especially γ-aluminium oxide. The catalyst may contain one or more of the hydrogenation-active metals.

The catalyst according to the invention preferably contains the metals copper, chromium, nickel. The catalyst particularly preferably contains the combination of the three metals copper, chromium and nickel as hydrogenation-active metal.

The total content of hydrogenation-active metals, based on the reduced catalyst, is in the range from 1 to 40% by mass, especially in the range from 5 to 25% by mass, calculated as the metal.

The catalysts according to the invention are prepared advantageously in a form which produces low flow resistance in the hydrogenation, such as for example tablets, cylinders, strand extrudates or rings. In the course of preparation of the catalyst, the preliminary support material is typically made into the appropriate form. Moulded preliminary support material is also commercially available.

In the method according to the invention, the hydrogenation can be carried out continuously or batchwise over finely divided or moulded catalysts arranged suspended in the fixed bed. Preference is given to continuous hydrogenation over a catalyst arranged in the fixed bed in which the product/reactant phase is mainly in the liquid state under the reaction conditions.

If the hydrogenation is carried out continuously over a catalyst arranged in the fixed bed, it is advantageous to convert the catalyst to the active form prior to the hydrogenation. This can be effected by reduction of the catalyst using hydrogen-containing gases according to a temperature programme. In this case, the reduction may be carried out optionally in the presence of a liquid phase which is passed over the catalyst, such as described, for example, in DE 199 33 348.

The hydrogenation method according to the invention is carried out in the trickle phase or preferably in the liquid phase in triphase reactors in cocurrent, wherein the hydrogen is finely distributed in a manner known per se in the liquid reactant/product stream. In the interests of a uniform liquid distribution, of improved removal of heat of reaction and of a high space-time yield, the reactors are preferably operated with high liquid loadings of 15 to 120, especially of 25 to 80 $m^3$ per $m^2$ of cross section of the empty reactor and per hour. When a reactor is operated isothermally and in straight pass, the specific liquid hourly space velocity (LHSV) may assume values between 0.1 and 10 $h^{-1}$.

The method according to the invention is carried out with hydrogen in a pressure range from 5 to 100 bar, preferably between 5 and 40 bar, particularly preferably in the range from 10 to 25 bar. The hydrogenation temperatures are between 120 and 220° C., especially between 140 and 190° C.

The hydrogen used for the hydrogenation may contain inert gases such as methane or nitrogen for example. Preference is given to using hydrogen having a purity of greater than 98%, especially greater than 99%.

For the method according to the invention, various method variants may be selected. The method can be carried out single-stage or multistage, adiabatically or practically isothermally, i.e. with a temperature increase of less than 10° C. In the latter case, all reactors, advantageously tubular reactors, may be operated adiabatically or practically isothermally and also one or more adiabatically and the others practically isothermally. It is also possible to hydrogenate the carbonyl compounds or mixtures of carbonyl compounds in the presence of water in straight pass or with product recycling.

In addition to the α,β-unsaturated $C_{2n}$-aldehydes and the unreacted $C_n$ starting aldehydes in the aldolization, the hydrogenation also converts the $C_n$ aldehydes having a higher proportion of branched aldehydes present in the second stream (1b) to the corresponding alcohols.

According to the invention, the separation of the mixture of saturated $C_n$ and $C_{2n}$ alcohols follows on from the hydrogenation according to step f), in which in this case the separation of the $C_n$-alcohols and the $C_{2n}$-alcohols may be effected by various combinations of classical distillation columns or dividing wall columns, or a combination of both column types, by means of at least one two-column system or by means of at least one dividing wall column.

In a particularly preferred embodiment of the present invention, a two-column system or a dividing wall column is used in order in both cases to obtain the $C_n$- and $C_{2n}$-alcohols as products of value.

The various method variants are described in more detail below.

In one embodiment of the present invention, at least one two-column system is used. In the first column, in the course of the method, alkanes formed (in the case of butenes mainly nonane), together with the $C_n$-alcohol (for example 2-methylbutanol) and water, are taken via the overhead. Phase separation takes place there and the organic phase is fed again to the column as return stream. By means of this azeotrope drying, the water content in the bottoms is obtained at less than 1000 ppm. In the second column, the $C_n$ alcohol is taken via the overhead and thus separated from the high boilers. By means of appropriate mode of operation of the column, the isomeric composition of the C5 alcohols may additionally be controlled.

FIG. 2 shows the detailed sequence of the separation of the mixture of $C_n$ and $C_{2n}$-alcohols by means of a two-column system which is subdivided into the following substeps:

I. Distillative separation (G) of the crude product stream of the hydrogenation (3) from step e) into a low-boiler stream (6) and a high-boiler stream (15). In this case, the low-boiler stream (6) comprises as main product the alcohols of the starting aldehydes and further substances or azeotropes having a lower boiling point than the alcohols formed from the α,β-unsaturated $C_{2n}$-aldehydes and heterogeneous water. The high-boiler stream (15) comprises as main product the alcohols formed from the α,β-unsaturated $C_{2n}$-aldehydes and high-boilers or azeotropes having a higher boiling point than the $C_{2n}$-alcohols.

II. Removal of the heterogeneous water (7) from the distillate fraction (6) via separator (F).

III. Distillative separation (H) of the organic phase (8) from F into a low-boiler stream (9) and a high-boiler stream (12). The low-boiler stream (9) comprises substances or azeotropes having a lower boiling point than the highest boiling $C_n$-alcohol and may contain heterogeneous water (11) after condensation. The high-boiler stream mainly comprises the $C_n$-alcohols and substances or azeotropes having a higher boiling point than the highest boiling $C_n$-alcohol.

IV. Removal of the heterogeneous water (11) by phase separation (E). The organic phase is fed again as return stream (19) to column (H). A portion of the organic phase (10) obtained is driven from the system.

V. Distillative separation (I) of the high-boiler stream (12) into a low-boiler stream (4) and a high-boiler stream (14). The low-boiler stream (4) mainly comprises the $C_n$-alcohol with the desired isomer distribution. The high-boiler stream (14) mainly comprises substances or azeotropes having a higher boiling point than the highest boiling $C_n$-alcohol.

VI. Distillative separation of the high-boiler stream (15) into a low-boiler stream (5), which comprises the $C_{2n}$-alcohols, and a high-boiler stream (18). The low-boiler stream (5) mainly comprises the $C_{2n}$-alcohol. The high-boiler stream (18) mainly comprises substances or azeotropes having a higher boiling point than the highest boiling $C_{2n}$-alcohol.

The temperature profiles used in the columns are adjusted in each case depending on the respective composition of the product stream from the hydrogenation (step b) of the method according to the invention.

For example, the product stream (3) may have the following composition:

| | |
|---|---|
| 2-Propylheptenal (% by mass) | 0.9 |
| n-Pentanol (% by mass) | 2.8 |
| 2-Methylbutanol (% by mass) | 2.8 |
| 2-Propylheptanol (% by mass) | 87.5 |
| 2-Propyl-4-methylhexanol (% by mass) | 4.2 |
| $H_2O$ | 1.7 |

In the case of this composition, column (G) is operated preferably at a top pressure of 0.2 bar(abs) and a pressure drop of 0.1 bar, and a bottom temperature of 176° C. and a top temperature of 65° C. are to be maintained, or corresponding equivalents. Column (H) is operated particularly at a top pressure of 1.05 bar(abs) and a pressure drop of 0.03 bar at a bottom temperature of 137° C. and a top temperature of 94° C., or corresponding equivalents. Column (I) is generally to be maintained at a top pressure of 1.08 bar(abs) and a pressure difference of 0.03 bar at a bottom temperature of 178° C. and a top temperature of 134° C., or corresponding equivalents.

Column (J) is operated ata pressure of 0.15 bar(abs) and a pressure difference of 0.006 bar at a bottom temperature of 175° C. and a top temperature of 158° C., or corresponding equivalents. The temperature profiles specified are to be considered as exemplary. Further configurations, especially in connection with varying feed compositions, are included in the context of the present invention.

In a further likewise preferred embodiment of the present invention, at least one dividing wall column is used. In a dividing wall column, the separating operations described for the two-column system can be combined in one column. The example of alkane/2-methylbutanol/water mixture is also obtained via the overhead, is subjected to an analogous phase separation and the organic phase is fed back again to the column as return stream. Via a side take-off in the region of the dividing wall, the Co-alcohol that meets the specification is drawn off. The isomer ratio of the Co-alcohol in the side take-off may be controlled within certain limits via the reduction in the distillate of the organic phase and the proportion of alcohol in the bottom of the column. FIG. 3 depicts the sequence when using a dividing wall column (K) for separating the low-boiler stream (6).

In this context, the columns H and I depicted in FIG. 2 are combined to form a dividing wall column (K) (see FIG. 3). The dividing wall column (K) is to be maintained at a top pressure of 1.05 bar(abs) and a pressure drop of 0.06 bar, a bottom temperature of 180° C., a top temperature of 118° C. and a product temperature of 134° C., or corresponding equivalents.

Figure 4:
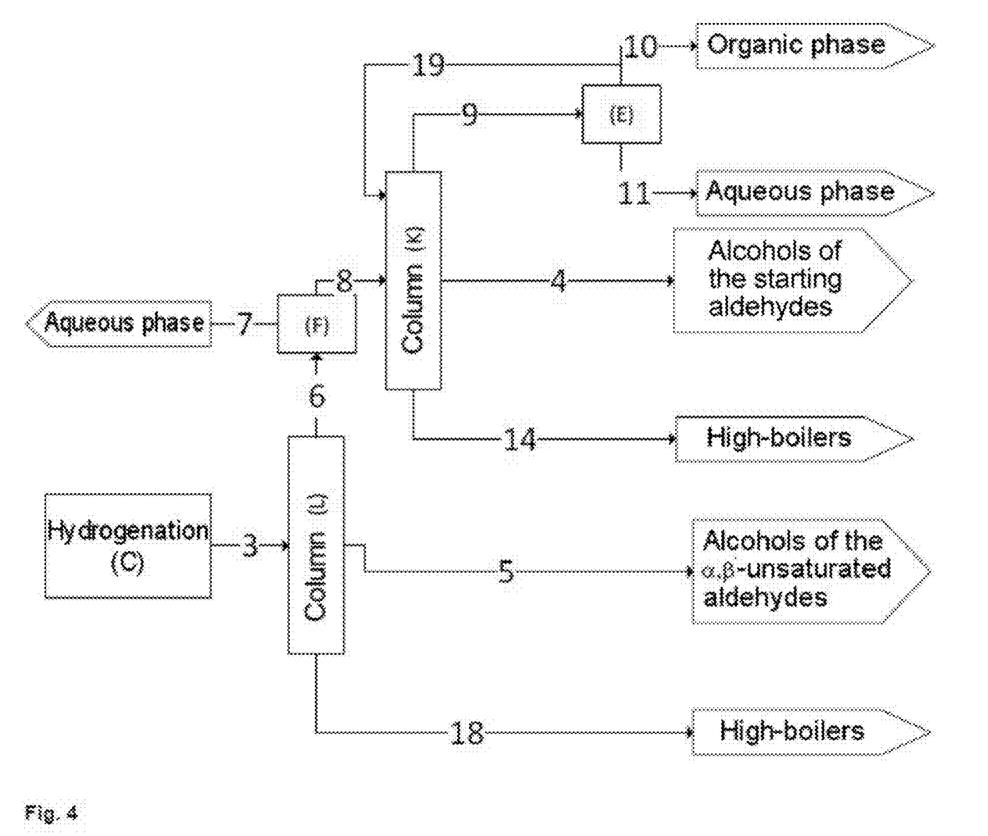
FIG. 4 is a schematic of a method according to one or more embodiments described herein.

FIG. 4 shows a further preferred embodiment, in which the separation of the crude product stream from the hydrogenation e) is also achieved by a dividing wall column. In this case, the $C_{2n}$-alcohol is drawn off via a side take-off in the region of the dividing wall.

The method according to the invention is suitable in an advantageous manner for the production of $C_n$- and $C_{2n}$-alcohols from aldehydes and in the case of upstream hydroformylation from olefins.

In the case of the isomeric $C_n$-aldehydes used where n=4, 5 and 6, n=5 is especially preferred. As already discussed above, such aldehydes may be obtained by hydroformylation of corresponding isomeric olefins. In the latter case, these are particularly olefins having 3 to 5 carbon atoms, namely propenes, butenes and pentenes, wherein the respective positional isomers (in the case of butenes and pentenes) are included by means of the designations specified. The isomeric olefins are particularly preferably butenes. In the latter case, these are converted by the method according to the invention to pentanol mixtures and decanol mixtures.

With regard to plasticizer syntheses, the isomer distributions of the pentanol mixtures are of particular interest.

By way of example and as a preferred embodiment, the pentanol mixture obtained preferably comprises less than 60 mol % n-pentanol. The minimum content of n-pentanol in the mixture of isomeric pentanols is preferably at least 2 mol %, preferably at least 10 mol %, more preferably more than 20 mol %, with more preference more than 22.5 mol % or even more than 25 mol %, more preferably more than 27.5 mol %, 30 mol % or even more than 35 mol %. In addition to the linear n-pentyl radicals, particular preference is given to pentanols comprising branched pentyl radicals. A branched pentyl radical is preferably a methylbutyl radical. Accordingly, preference is given to a pentanol mixture in which the branched pentyl radicals consist of methylbutyl radicals to an extent of at least 50 mol %, preferably to an extent of at least 60 mol %, further preferably to an extent of at least 70 mol %, still further preferably to an extent of at least 80 mol %, even more preferably to an extent of at least 90 mol % and especially to an extent of at least 95 mol %.

It is advantageous if the branched isomeric pentyl radicals have a large proportion of 2-methylbutyl radicals. In a preferred embodiment, therefore, at least 50 mol %, preferably at least 60 mol %, more preferably at least 70 mol %, further preferably at least 80 mol %, especially preferably at least 90 mol % and especially at least 95 mol % of the branched isomeric pentyl radicals are 2-methylbutyl radicals. The preferred pentanol mixtures preferably comprise 20 to 95 mol %, preferably 30 to 85 mol % and especially 40 to 75 mol % of 2-methylbutyl radicals, based on all pentyl radicals present.

In a particularly preferred embodiment, the pentanol mixture consists to an extent of at least 75 mol %, more preferably to an extent of at least 90 mol % and especially to an extent of at least 95 mol % of pentanols comprising—preferably exclusively—2-methylbutyl and/or linear pentyl radicals, where the molar ratio of 2-methylbutyl radicals to linear pentyl radicals in this pentanol mixture is preferably in the range from 99:1 to 40:60, especially in the range from 70:30 to 40:60.

The desired product properties, especially the isomer distributions mentioned above, are adjusted particularly by the partial isomer separation of the aldehydes described in method step b) by means of distillation and by the parameters for carrying out the separation of the mixture of $C_n$ and $C_{2n}$-alcohols by the two-column or dividing wall column systems used specified in step f).

Even without further elaboration it is believed that a person skilled in the art will be able to make the widest use of the above description. The preferred embodiments and examples are therefore to be interpreted merely as a descriptive disclosure which is by no means limiting in any way whatsoever. The present invention is elucidated in more detail below using examples. Alternative embodiments of the present invention are obtainable analogously.

EXAMPLES

For carrying out the examples and the determination of the respective parameters, the following basic assumptions were used, based on the $C_n/C_{2n}$ system where n=5.

The degree of conversion $Xi1$ and $Xi2$ were calculated by the following calculation method:

$$Xi1 = \frac{\%\text{ by mass } n-\text{pentanal reactant input} - \%\text{ by mass } n-\text{pentanal product output}}{\%\text{ by mass } n-\text{pentanal reactant input}}$$

$$Xi2 = \frac{\%\text{ by mass } 2-\text{methylbutanal reactant input} - \%\text{ by mass } 2-\text{methylbutanal product output}}{\%\text{ by mass } 2-\text{methylbutanal reactant input}}$$

The proportion of n-pentanal, based on the C5-aldehydes in the product (Sn1), was calculated by the following calculation method:

$$Sn1 = \frac{\%\text{ by mass } n-\text{pentanal reactant output}}{\%\text{ by mass } n-\text{pentanal product output} + \%\text{ by mass } 2-\text{methylbutanal product output}}$$

The proportion of 2-propylheptenal, based on the unsaturated C10-aldehydes in the product (Sn2), was calculated by the following calculation method:

$$Sn2 = \frac{\%\text{ by mass } 2-\text{propylheptenal}}{\%\text{ by mass } 2-\text{propylheptenal} + \%\text{ by mass } 4-\text{propyl}-4-\text{methylhexenal}}$$

The chemical compositions in the examples were determined by gas chromatography. For this purpose, a 7890A gas chromatograph from Agilent was used with a flame ionization detector (FID). The column used was an HP-5 (5% phenylmethylsiloxane) 325° C. 30 m×320 μm×0.25 μm. The following temperature programme was applied for the analysis: 2 min at 50° C., then to 150° C. at 10° C./min then at 40° C./min to 250° C. with a 10 min holding phase. Injection volumes 0.5 μl. Injector temperature 250° C. nitrogen carrier gas at a flow rate of 105 ml/min and a split of 50:1.

Example 1

In order to assess the separation of a particular isomer ratio prior to the aldolization, simulation studies were conducted.

For the simulation, Aspen Plus V7.3 was used with the PSRK (predictive Soave-Redlich-Kwong) method. The column is simulated as a Radfrac model and is configured such that separation of the overhead product with an n-pentanal fraction of 30% up to 70% is possible. In particular, an n-pentanal fraction of 50% should be considered. In addition, the bottom product should contain an n-pentanal fraction of 95-100%. To achieve the isomer distribution, a column with 50 theoretical plates is used. For the calculations, the following starting concentration is considered, which is metered in in the liquid state. The results of the column simulation are also presented.

| | Feed Mass fraction [—] | Bottoms Mass fraction [—] | Overhead Mass fraction [—] |
|---|---|---|---|
| n-Butane | 0.00065603 | 0 | 0.011 |
| trans-2-Butene | 0.00015467 | 0 | 0.003 |
| cis-2-Butene | 0.00018928 | 0 | 0.003 |
| 2-Methylbutanal | 0.03286881 | 0.004 | 0.483 |
| n-Pentanal | 0.96607143 | 0.996 | 0.501 |

Example 2: Aldolization of n-Pentanal Including Condensation to α,β-Unsaturated C10 Aldehydes in a Stirred Reactor The α,β-unsaturated C10 aldehydes were prepared in a stirred reactor. This reactor took the form of an extraction column having a volume of 2.1 litres. The reactor was divided into ten mixing chambers and each of these mixing chambers was equipped with a 4-blade stirrer which were mounted on a common stirrer shaft. A catalyst phase was passed through the reactor in the circuit by a circuit pump. A 2% aqueous sodium hydroxide solution was used as catalyst phase. The catalyst circuit was 80 l/h in all experiments. The reactant comprised 98.3% by mass n-pentanal, the remaining proportions being made up of secondary components. The reactant was fed at 8 l/h continuously to the catalyst circuit just before the reactor inlet.

The biphasic mixture obtained at the reactor outlet was separated into an organic product phase and a catalyst phase in a phase separation vessel.

The system was operated under a nitrogen atmosphere at a pressure of 4 bar and, after three hours steady-state operation, the following results were determined.

| Reaction conditions | |
| --- | --- |
| Stirrer speed rpm | 2000 |
| Temperature ° C. | 130 |
| Product composition | |
| n-Pentanal (% by mass) | 4.9 |
| 2-Propylheptenal (% by mass) | 91.3 |
| Remainder (incl. dissolved water) | 3.8 |
| Degree of conversion | |
| n-Pentanal | 0.95 |
| Starting organic phase kg/h | 5.8 |
| Mass stream of pentanal kg/h | 0.3 |
| Mass stream of 2-propylheptenal kg/h | 5.8 |

Example 3: Aldolization of n-Pentanal and 2-Methylbutanal Including Condensation to α,β-Unsaturated C10 Aldehydes in a Flow Tube The α,β-unsaturated C10 aldehydes were prepared in a three meter length DN15 tube having an internal diameter of 17.3 mm. This tube had a volume of 6.8 litres. Circa 50% of the total volume was filled with static mixers with a channel diameter of 2 mm. The mixing elements are formed from serrated lamellae which form open crossing channels. The channels are arranged in the tube at a distance of one mixing length offset by 90° from one another. With the aid of a pump, a continuous circulation of a catalyst phase of 80 l/h was established through this tube. A 2.1% aqueous sodium hydroxide solution was used as catalyst phase.

The reactant comprised 98.7% by mass n-pentanal, the remaining proportions up to 100% being composed of secondary components. The reactant was fed continuously at 8 l/h to the catalyst circuit briefly before the start of the static mixers.

The biphasic mixture obtained at the reactor outlet was separated into an organic product phase and a catalyst phase in a phase separation vessel.

The system was operated under a nitrogen atmosphere at a pressure of 4 bar and, after three hours steady-state operation, the following results were determined.

| Reaction conditions | |
| --- | --- |
| Temperature ° C. | 130 |
| Product composition | |
| n-Pentanal (% by mass) | 2.9 |
| 2-Propylheptenal (% by mass) | 93.3 |
| Remainder (incl. dissolved water) | 2.8 |
| Degree of conversion of n-pentanal (Xi1) | 0.97 |

Example 4

The reactant produced from example 3 was mixed with a C5 aldehyde mixture consisting of 50% by mass n-pentanal and 50% by mass 2-methylbutanal in such a way that, subsequently, approx. 7.3% of the C5 aldehyde mixture and 92.7% of the aldol condensation product are present in the feed mass.

This mixture was then subjected to hydrogenation. For the hydrogenation, a circulation system analogous to DE102009045718A1 example 1 was used. Analogous thereto, 105 g of catalyst were used composed of Cu (6% by mass)/Ni (3.1% by mass)/Cr (0.6% by mass) on Al2O3 as strand extrudate of 1.5 mm diameter and a length of 3-5 mm.

The reaction conditions were 180° C. and 25 bar absolute. The reactant feed was 100 ml/h at a circulation rate of 40 l/h and an offgas rate of 60 Nl/h.

| | 7.3% C5-Aldehyde/92.7% aldolization product | |
| --- | --- | --- |
| Composition | Feed | Product |
| n-Pentanal (% by mass) | 6.3 | 0.1 |
| 2-Methylbutanal (% by mass) | 3.7 | 0.0* |
| 2-Propylheptenal (% by mass) | 87.3 | 0.9 |
| 4-Propyl-4-methylhexanal (% by mass) | 0.0* | 0.0* |
| n-Pentanol (% by mass) | 0.0* | 6.2 |
| 2-Methylbutanol (% by mass) | 0.0* | 3.6 |
| 2-Propylheptanol (% by mass) | 0.0* | 85.6 |
| 4-Propyl-4-methylhexanol (% by mass) | 0.0* | 3.6 |
| Remainder | 2.7 | 3.6 |
| n-Pentanol proportion based on the C5-alcohols in the product | | 0.63 |
| 2-Propylheptanol proportion based on the C10- alcohols in the product | | 1.0 |

*below detection limit

Example 5

For assessment of the purification of the product stream from the hydrogenation, simulation studies were conducted. For this purpose, a product stream consisting of C10 and C5 alcohols is separated into individual fractions according to FIG. 2. Used for this purpose was Aspen Plus V7.3 using the PSRK (predictive Soave-Redlich-Kwong) method. The columns are simulated as Radfrac models and the columns are configured such that separation of the products at a purity of ca. 99.9% is possible. To achieve the product qualities, four columns with different specifications are provided.

| | Theoretical plates |
| --- | --- |
| Column I | 65 |
| Column II | 20 |
| Column III | 10 |
| Column IV | 55 |

By adding water (in the feed of column I), the separation of low-boilers is favoured. The water therefore does not accumulate in the columns and an aqueous phase is formed; water is removed at the top of each column into a decanter.

| | Feed | Product stream 1 (Alcohol from α,β-aldehydes) | Product stream 2 (Alcohol from starting aldehydes) |
| --- | --- | --- | --- |
| 2-Propylheptenal (% by mass) | 0.9 | 0 | 0 |
| n-Pentanol (% by mass) | 2.8 | 0 | 55.5 |
| 2-Methylbutanol (% by mass) | 2.8 | 0 | 44.4 |
| 2-Propylheptanol (% by mass) | 87.5 | 95.4 | 0 |
| 2-Propyl-4-methylhexanol (% by mass) | 4.2 | 4.6 | 0 |
| H2O | 1.7 | 0 | 0 |

Example 6

As an alternative to the separation using 4 columns, the separation may be carried out with the aid of dividing wall columns (likewise simulated using Aspen Plus V7.3, PSRK and Radfrac). For example, if column 2 and 3 are replaced by a 31 stage dividing wall column, the alcohol of the starting aldehydes may be drawn off as middle fraction.

The dividing wall extends in this case across 14 of the 31 plates. The product is discharged on the 15th stage. The vapour stream impinging on the dividing wall from below is fed in equal portions to the two column segments, whereas 75% of the liquid stream is passed to the product side and 25% to the feed side.

If the overhead product of column 1 is passed to the dividing wall column, the following product distribution arises:

|  | Feed to the dividing wall column | Product (sidestream of the dividing wall column) |
|---|---|---|
| $H_2O$ (% by mass) | 7.4 | 0 |
| n-Pentanol (% by mass) | 39.3 | 66.9 |
| 2-Methylbutanol (% by mass) | 39.5 | 33.1 |
| 2-Propylheptanol (% by mass) | 0 | 0 |
| 2-Propyl-4-methylhexanol (% by mass) | 0.6 | 0 |
| 2-Propylheptenal (% by mass) | 13.2 | 0 |

The results show that control of the amounts of $C_n$ alcohol and $C_{2n}$ alcohol with the procedure described is possible and the isomer distribution of $C_n$ can also be controlled in a corresponding manner.

LIST OF REFERENCE SYMBOLS

1 Hydroformylation product
1a Stream having a higher proportion of linear aldehydes than the hydroformylation product
1b Stream having a higher proportion of branched aldehydes than the hydroformylation product
2 Mixture of aldol condensation product and stream having a higher proportion of branched aldehydes than the hydroformylation product
3 Hydrogenation product (for example where n=5 largely water, butane, butene, $C_5$-aldehydes, 2-methylbutanol, pentanol, nonane, $\alpha,\beta$-unsaturated $C_{10}$ aldehydes, $C_{10}$-aldehydes, $\alpha,\beta$-unsaturated $C_{10}$-alcohols, $C_{10}$-alcohols, C10-oligomers having more than 10 carbon atoms)
4 $C_n$-alcohol (for example where n=5 largely 2-methylbutanol, pentanol)
5 $C_{2n}$-alcohol (for example where n=5 largely $C_{10}$-alcohols)
6 Low-boiler stream depleted in $C_{10}$-alcohol with proportions of heterogeneous water (for example where n=5 largely water (heterogeneous), butane, butene, $C_5$-aldehydes, 2-methylbutanol, pentanol, nonane, $\alpha,\beta$-unsaturated $C_{10}$ aldehydes, $C_{10}$-aldehydes, $\alpha,\beta$-unsaturated $C_{10}$-alcohols)
7 Aqueous phase
8 Organic phase depleted in $C_{10}$-alcohol with proportions of homogeneous water (for example where n=5 largely water (homogeneous), butane, butene, $C_5$-aldehydes, 2-methylbutanol, pentanol, nonane, $\alpha,\beta$-unsaturated $C_{10}$ aldehydes, $C_{10}$-aldehydes, $\alpha,\beta$-unsaturated $C_{10}$-alcohols)
9 Low-boiler stream (for example where n=5 largely water (homogeneous), butane, butene, $C_5$-aldehydes, 2-methylbutanol, pentanol, nonane)
10 Organic phase with homogeneous water (for example where n=5 largely water (homogeneous), butane, butene, $C_5$-aldehydes, 2-methylbutanol, pentanol, nonane)
11 Aqueous phase
12 High-boiler stream (for example where n=5 largely 2-methylbutanol, pentanol, $\alpha,\beta$-unsaturated $C_{10}$ aldehydes, $C_{10}$-aldehydes, $\alpha,\beta$-unsaturated $C_{10}$-alcohols)
14 High-boiler stream (for example where n=5 largely $\alpha,\beta$-unsaturated $C_{10}$ aldehydes, $C_{10}$-aldehydes, $\alpha,\beta$-unsaturated $C_{10}$-alcohols)
15 High-boiler stream (for example where n=5 largely $C_{10}$-alcohols, C10+-oligomers having more than 10 carbon atoms)
18 High-boiler stream (for example where n=5 largely C10+-oligomers having more than 10 carbon atoms)
19 Return stream

The invention claimed is:
1. A method for preparing saturated $C_n$- and $C_{2n}$-alcohols where n=4, 5 and 6, the method comprising the method steps of
   a) providing a mixture of isomeric $C_n$-aldehydes comprising unbranched aldehydes, wherein the proportion of unbranched aldehydes is at least 20% by weight, based on the $C_n$-aldehydes, wherein the $C_n$-aldehydes were prepared by hydroformylation of isomeric olefins having 3 to 5 carbon atoms with synthesis gas in the presence of a hydroformylation catalyst to form the aldehydes specified, and wherein the proportion of unbranched aldehydes is from 40 to 99.5% by weight, based on the $C_n$-aldehydes, wherein the hydroformylation comprises a catalyst system comprising rhodium as central atom and is complexed with the ligand (1)

and an organic amine of formula (2)

in which Ra, Rb, Rc, Rd, Re and Rf represent identical or different hydrocarbon radicals which may also be bonded to one another,
   b) carrying out a distillation for the at least partial separation of the isomeric $C_n$ aldehydes into a first stream having a higher proportion of linear aldehydes than the mixture provided in a) and into a second stream having a higher proportion of branched aldehydes than the mixture provided in a), c) carrying out an aldol condensation in a tubular reactor of the aldehydes present in the first stream having a higher proportion of linear aldehydes than the mixture provided in a) to obtain a mixture of $C_n$- and α,β-unsaturated $C_{2n}$-aldehydes wherein the tubular reactor comprises a mixing module which disperses the reactant aldehyde into droplets having an average diameter (Sauter diameter) of 0.2 mm to 2 mm in a process liquor comprising aqueous sodium hydroxide solution and sodium salts of carboxylic acids and has a sodium content of 0.6 to 1.75%, d) mixing the mixture of $C_n$- and α,β-unsaturated $C_{2n}$-aldehydes obtained in c) with the second stream, provided in b), having a higher proportion of branched $C_n$ aldehydes than the mixture provided in a), e) hydrogenating the mixture of $C_n$- and α,β-unsaturated $C_{2n}$-aldehydes and $C_n$-aldehydes obtained in d) with hydrogen to obtain a mixture of saturated $C_n$ and $C_{2n}$-alcohols, and f) separating the mixture of $C_n$ and $C_{2n}$-alcohols.

2. The method according to claim 1, wherein the ligand (1) is 3,3'-di-tert-butyl-5,5'-dimethoxy-[1,1'-biphenyl]-2,2'-diyltetrakis(2,4-dimethylphenyl)bis(phosphite).

3. The method according to claim 2, wherein the organic amine comprises at least one 2,2,6,6-tetramethylpiperidine 4. The method according to claim 1, wherein the aldol condensation in step a) is carried out in the presence of aqueous sodium hydroxide solution, and wherein the proportion of unbranched aldehydes is from 95 to 99.5% by weight, based on the $C_n$-aldehydes.

5. The method according to claim 1, wherein the process liquor has a pH in the range from 12.5 to 13.5.

6. The method according to claim 1, wherein the aldol condensation of the $C_n$-aldehydes according to step a) is carried out in a temperature range from 100 to 150° C.

7. The method according to claim 1, wherein a reaction pressure in the tubular reactor during the aldol condensation of the $C_n$-aldehydes according to step a) is in a range from 0.2 to 1.0 MPa.

8. The method according to claim 1, wherein the hydrogenation according to step b) is carried out in a temperature range from 170° C. to 200° C. at a pressure of $15*10^5$ Pa to $30*10^5$ Pa over a supported catalyst which contains at least nickel and copper as active components.

9. The method according to claim 1, wherein the hydrogenation according to step b) is carried out with hydrogen in a pressure range from 5 to 100 bar and the hydrogenation temperatures are between 120 and 220° C.

10. The method according to claim 1 wherein n=5.

11. The method according to claim 2, wherein the aldol condensation in step a) is carried out in the presence of aqueous sodium hydroxide solution.

12. The method according to claim 3, wherein the aldol condensation in step a) is carried out in the presence of aqueous sodium hydroxide solution.

13. The method according to claim 2, wherein the process liquor has a sodium content of 1.1 to 1.20% by mass and a pH in the range from 12.5 to 13.5.

14. The method according to claim 3, wherein the process liquor has a sodium content of 1.1 to 1.20% by mass and a pH in the range from 12.5 to 13.5.

15. The method according to claim 2, wherein the aldol condensation of the $C_n$-aldehydes according to step a) is carried out in a temperature range from 100 to 150° C.

16. The method according to claim 3, wherein the aldol condensation of the $C_n$-aldehydes according to step a) is carried out in a temperature range from 100 to 150° C.

17. The method according to claim 2, wherein a reaction pressure in the tubular reactor during the aldol condensation of the $C_n$-aldehydes according to step a) is in a range from 0.2 to 1.0 MPa.

18. The method according to claim 2, wherein the hydrogenation according to step b) is carried out in a temperature range from 170° C. to 200° C. at a pressure of $15*10^5$ Pa to $30*10^5$ Pa over a supported catalyst which contains at least nickel and copper as active components.

19. The method according to claim 1, wherein the hydrogenation according to step b) is carried out with hydrogen in a pressure range from 5 to 100 bar and the hydrogenation temperatures are between 120 and 220° C.

20. The method according to claim 2, wherein n=5.

* * * * *